(12) United States Patent
Gaillac et al.

(10) Patent No.: US 7,378,265 B2
(45) Date of Patent: May 27, 2008

(54) METHOD OF INACTIVATING ENVELOPED VIRUSES IN A VIRAL PREPARATION OF NON-ENVELOPED VIRUSES

(75) Inventors: David Gaillac, Thiais (FR); Michel Koehl, Strasbourg (FR)

(73) Assignee: Transgene S.A., Strasbourg (FR)

( * ) Notice: Subject to any disclaimer, the term of this patent is extended or adjusted under 35 U.S.C. 154(b) by 350 days.

(21) Appl. No.: 11/301,160

(22) Filed: Dec. 12, 2005

(65) Prior Publication Data

US 2006/0166345 A1 Jul. 27, 2006

Related U.S. Application Data

(62) Division of application No. 09/467,928, filed on Dec. 21, 1999, now Pat. No. 7,026,154.

(30) Foreign Application Priority Data

Dec. 21, 1998 (FR) .................................. 98 16147

(51) Int. Cl.
*C12N 7/04* (2006.01)
(52) U.S. Cl. ..................................... 435/236
(58) Field of Classification Search ................. 435/236
See application file for complete search history.

(56) References Cited

U.S. PATENT DOCUMENTS 6,281,010 B1 8/2001 Gao et al.

FOREIGN PATENT DOCUMENTS

| EP | 378208 A2 | 7/1990 |
| EP | 812858 A1 | 12/1997 |
| WO | 94/28152 | 12/1994 |
| WO | 98/26048 | 6/1998 |
| WO | 98/39420 | 9/1998 |

OTHER PUBLICATIONS

Huyghe, Bernard G. et al. (1995). *Human Gene Therapy*, 6:1403-1416.
Kopecka, Helena, "Echoviruses", Encyclopedia of Virology, pp. 354-360.
Melnick, Joseph L. (1990). "Enteroviruses: Polioviruses, Coxsackieviruses, Echoviruses, and Newer Enteroviruses", *Fields Virology* 2nd Ed., Ch 21, pp. 549-551, Raven Press Ltd., New York, NY, USA.

*Primary Examiner*—J. S. Parkin
(74) *Attorney, Agent, or Firm*—Buchanan, Ingersoll & Rooney, P.C.

(57) ABSTRACT

The present invention relates to a method of inactivating enveloped viruses in a viral preparation predominantly containing non-enveloped viruses by the action of a solvent at a temperature of between −5° C. and +50° C. and at a pH of between about 5 and 9. Its subject is also a method of preparing a viral preparation comprising such a method of inactivation. The invention also relates to a viral preparation obtained according to the method of the invention. Finally, it relates to a host cell and a composition comprising such a viral preparation as well as their uses for therapeutic or prophylactic purposes.

29 Claims, No Drawings

METHOD OF INACTIVATING ENVELOPED VIRUSES IN A VIRAL PREPARATION OF NON-ENVELOPED VIRUSES

This application is a divisional of U.S. patent application Ser. No. 09/467,928, filed Dec. 21, 1999, now U.S. Pat. No. 7,026,154.

The present invention relates to a method of inactivating enveloped viruses capable of contaminating a viral preparation based on non-enveloped viruses. The subject of the invention is also a viral preparation which is essentially free of enveloped viruses and a pharmaceutical composition comprising such a viral preparation as well as their uses for therapeutic or prophylactic purposes. The present invention is of particular importance in the perspective of gene therapy, in particular in humans.

Gene therapy is defined as the transfer of genetic information into a cell or a host organism. The first protocol applied to humans was initiated in the United States in September 1990 on a patient who was genetically immunodeficient because of a mutation affecting the gene encoding Adenine Deaminase (ADA). It involved correcting or replacing the defective gene, whose dysfunction is responsible for a genetic disease, with a functional gene. The relative success of this first experiment encouraged the development of this technology, which has since been extended to the treatment of other disease, both genetic and acquired (cancers, infectious diseases such as AIDS and the like) with the aim of delivering in situ therapeutic genes which improve the pathological condition. Most of the strategies use vectors to carry the therapeutic gene to its target cell. Many vectors, both viral and synthetic, have been developed during the past few years and have been the subject of many publications accessible to persons skilled in the art.

The importance of adenoviruses as vectors for gene therapy has already been mentioned in the prior art. They infect many cell types, both dividing and quiescent cells, are non-integrative and are not highly pathogenic. In addition, they possess a natural tropism for the respiratory tracts. These special properties make adenoviruses preferred vectors for many therapeutic and even vaccine applications.

The infectious cycle for adenoviruses occurs in two stages. The early phase precedes the initiation of replication and makes it possible to produce the early proteins which regulate the replication and the transcription of the viral DNA. The replication of the genome is followed by the late phase during which the structural proteins, which constitute the viral particles, are synthesized. The assembly of the new virions takes place in the nucleus. In the first stage, the viral proteins assemble so as to form empty capsids of icosahedral structure into which the genome is encapsidated. The adenoviruses released are capable of infecting other permissive cells.

As a guide, their genome consists of a linear and double-stranded DNA molecule of about 36 kb which carries about thirty genes which are involved in the viral cycle. The early genes (E1 to E4; E for early) are distributed over four regions dispersed in the genome. The E1, E2 and E4 regions are essential for viral replication whereas the E3 region, which is involved in modulating the anti-adenovirus immune response in the host, is not. The late genes (L1 to L5; L for late) predominantly encode the structural proteins and partly cover the early transcriptional units. They are for the most part transcribed from the major late promoter MLP (for Major Late Promoter). In addition, the adenoviral genome carries at its ends cis acting regions which are essential for the encapsidation and which consist of inverted terminal sequences (ITR) situated at the 5' and 3' ends and of an encapsidation region which follows the 5' ITR.

The adenoviral vectors currently used in gene therapy protocols lack most of the EI region so as to avoid their dissemination into the environment and the host organism. Additional deletions in the E3 region make it possible to increase the cloning capacities. So-called second-generation vectors are also available. They conserve the regions in cis (ITRs and encapsidation sequences) which are essential for the encapsidation but comprise additional genetic modifications aimed at reducing the in vivo expression of certain viral genes capable of hampering the persistence of the transduced cells and the stable expression of the transgene (see for example international applications WO94/28152 and WO97/04119). In this regard, a minimum vector, which is deficient for all the adenoviral functions, represents a preferred alternative.

For obvious safety reasons, it is important to obtain viral preparations free of potentially harmful contaminants. The recombinant adenoviruses are usually produced in a cell line complementing the defective functions. After culture, the infected cells are harvested, lysed and the viral particles are purified from the cell lysate. Most teams working in this field have been interested in reducing the molecular contaminants (protein, DNA, inorganic or toxin contaminants and the like) using caesium chloride gradient ultracentrifugation or chromatographic techniques. However, potential contamination with other types of viruses has remained unsolved up until now. In this regard, the pathological risks associated with enveloped viruses are not without consequences since they can lead to cancers, hepatitis, AIDS and the like. It is therefore crucial that the recombinant virus preparations intended for human use are free of infectious enveloped viruses.

However, the sources of contamination are many throughout the method which leads to the preparation of the viruses of interest. In addition to accidental contamination, the cell lines used to propagate the viruses of interest may comprise, integrated into their chromosomes, a number of retroviral genomes (proviruses). These may be activated in response to certain culture conditions, generating infectious enveloped viruses. Furthermore, the culture media frequently contain serum of animal origin which is a major source of enveloped viruses. Furthermore, the operators, the environment and the equipment for multiple use (fermenter, homogenizer, chromatographic column and the like) may also contribute to the contamination. These contaminants are called foreign agents and comprise enveloped viruses, but also bacteria and cells.

A method of inactivating enveloped viruses with a mixture of tri(n-butyl) phosphate (TNBP) has already been used for the preparation of blood proteins and derivatives (platelet concentrates, cryoprecipitates, fractionation products and the like) where contamination with the hepatitis B viruses constitutes a major public health problem. Such a method has never been applied to a preparation of non-enveloped viruses where contamination with enveloped viruses acts against the safety of the clinical batches.

Unlike the prior art method, which is applicable to protein compositions, there is the particular problem of the coexistence of two viral types in the same preparation, on the one hand the non-enveloped viruses which it is desirable to preserve and the enveloped viruses whose inactivation is sought. A method according to the invention must reconcile these two prerequisites. In general, viruses have a complex structural architecture and the integrity of the viral particle is essential for infectivity and penetration into the host cells.

In this regard, adenoviruses are composed of a DNA molecule associated with proteins and surrounded by an icosahedral capsid. The capsid consists of capsomers comprising 720 hexons and 60 pentons which are associated with monomers of polypeptides IIIa, IV and IX which stabilize the structure. Bound to the penton subunit and extending outside of the capsid is the trimeric fibre which allows the initial attachment of the virus to its target cell. A slightly impaired adenoviral capsid can have a harmful effect on viral infectivity. The fragility of adenoviruses can be illustrated by mentioning the fact that prolonged exposure to a temperature greater than 37° C. is sufficient to reduce the infectious power often by several log units.

A method of inactivating enveloped viruses in a preparation containing recombinant adenoviruses as active ingredients has now been developed which uses the solvent tri-n-butyl phosphate (TNBP). Moreover, the effect of different variables has been studied in order to define the experimental conditions most appropriate for preserving the infectivity of the recombinant adenoviruses and so as to become integrated in an overall method of purification. The examples which follow show that the action of 0.1 to 0.6% TNBP and of 1% to 2% Tween® 80 for 4 h at room temperature makes it possible to significantly reduce the quantity of enveloped viruses (reduction by a factor of at least 4 log units) while preserving the integrity of the adenoviral particles (yield of at least 80%, or even greater than 100%). The beneficial effect of the method according to the invention for reducing the aggregates which spontaneously form between the virions and hamper the infectivity of the viruses has also been demonstrated.

Accordingly, the subject of the present invention is a method of inactivating enveloped viruses in a viral preparation predominantly containing non-enveloped viruses, according to which a sufficient quantity of a solvent is introduced into the said viral preparation and the said solvent is allowed to act at a temperature of between about −5° C. and +50° C., at a pH of between about 5 and about 9 for a period which is sufficiently long to significantly reduce the quantity of enveloped viruses present in the said viral preparation.

"Enveloped viruses" and "non-enveloped viruses" are widely defined in basic virology manuals. Briefly, enveloped viruses have at their surface an envelope composed of a lipid layer or bilayer and of associated proteins. Its composition is due to the fact that it forms during the budding of the viruses through the cell membrane. The term cell membrane includes the plasm membrane and the membranes of the other cellular organelles such as the endoplasmic reticulum, the Golgi apparatus, the nucleus. In contrast, a non-enveloped virus does not possess any lipid at its surface and is surrounded by a protein capsid.

A "viral preparation" predominantly contains one or more non-enveloped viruses in an aqtieous medium (culture medium, buffered medium, formulation solution and the like). The term "virus" includes the wild-type, mutant and recombinant viruses (comprising at least one gene of interest). A viral preparation is usually produced by introducing the DNA of the non-enveloped virus carried by one or more fragments into an appropriate cell line or by infecting the line with a viral prestock. The infected transfected line is then cultured and the viral particles produced are harvested from the producing cells and/or the culture supernatant.

It should be stated that in the context of the present invention, the viral preparation may also be subjected to one or more purification steps aimed at achieving levels of purity which are compatible with the pharmaceutical quality required for the viral product (at least partial removal of the contaminants of the protein, toxin or nucleic acid type, and the like). The purification may be carried out by caesium chloride gradient centrifugation or chromatographic techniques such as those detailed below.

An advantageous embodiment of the present invention consists in the use of a non-enveloped virus defective for replication, in which one or more essential viral functions are made non-functional by mutation (addition, deletion and/or substitution of one or more continuous or non-continuous nucleotides).

The method of inactivation according to the invention is intended to reduce or eliminate the enveloped viruses capable of contaminating a viral preparation comprising one or more non-enveloped viruses of interest.

The term "inactivation" can be defined as a significant or complete reduction in the infectivity of the enveloped virus(es) contaminating the viral preparation of interest. For the purposes of the present invention, the infectivity is reduced by a factor of at least 2 log units, advantageously of at least 3 log units and preferably of at least 4 log units and more preferably of at least 7 log units. The inactivation of the enveloped viruses may be evaluated according to prior art techniques, for example by electron microscopy, HPLC, molecular biology methods (PCR), methods for titration of the viral titre, fluorescence, immunological methods (ELISA, RIA and the like), immunoenzymatic methods allowing the detection of one or more viral polypeptides (Western and the like), measurement of the reverse tranoscriptase activity in particular for retroviruses and the like.

For the purposes of the present invention, the solvent may be introduced into the viral preparation immediately after harvesting the non-enveloped viruses (unpurified viral preparation) or at any stage of its purification.

In the context of the present invention, the term "solvent" designates any substance, solution or composition capable of solubilizing a lipid or of dissociating a constituent comprising one or more lipids. In the present case, a solvent in use in the method according to the invention is more particularly intended to dissociate a viral envelope. Although any solvent can be envisaged, the use of Hecameg (Interchim reference UP785480), ether or an alkyl phosphate, alone or in combination, is nevertheless preferred. The combination may combine solvents of the same chemical family (for example two alkyl phosphates) or of different families (ether and alkyl phosphate). In the context of the present invention, the solvent is more particularly chosen from the group consisting of dialkyl phosphates and trialkyl phosphates. Advantageously, each of the alkyl groups of the dialkyl or trialkyl phosphate independently comprises from 1 to 10 carbon atoms. The alkyl group(s) may be under linear or branched (isoalkyl) form and may possibly be substituted. It is preferably a trialkyl phosphate in which each of the 3 alkyl groups independently comprises from 2 to 8 carbon atoms, and most preferably from 3 to 5. Purely by way of illustration, there may be mentioned tri-(n-butyl) phosphate (TNBP), tri-(t-butyl) phosphate, tri-(n-hexyl) phosphate, tri-(2-ethylhexyl) phosphate, tri-(n-decyl) phosphate. A particularly preferred solvent is—tri-n-butyl phosphate.

The quantity of solvent to be used in the method according to the invention should be sufficient to significantly reduce the infectivity of the enveloped viruses contaminating the viral preparation of interest. Of course, the said quantity may vary as a function of certain parameters of the method according to the invention (volume of the viral preparation, level of contamination, type of enveloped viruses, state of purification of the viral preparation, and the like). Persons skilled in the art are capable of adjusting the quantity of solvent necessary to the precise experimental conditions. Advantageously, the solvent is used at a final concentration of between 0.001% and 10% (1% corresponding to 1 ml of a stock solution of solvent having a purity greater than 99% or to 1 g of pure solvent for a total volume of 100 ml). According to a preferred embodiment, the solvent introduced into the said viral preparation is tri-(n-butyl) phosphate and in a quantity of between 0.05% and 1%, preferably between 0.1% and 0.6% and most optimally in the region of 0.3%.

According to an optional but nevertheless advantageous embodiment, the method of inactivating enveloped viruses according to the invention is carried out in the presence of a detergent, a surfactant or an amphiphilic molecule, which is preferably nonionic. These terms, which are grouped together below under the name of solubilizing agent, designate any substance, solution or composition facilitating the solubility of another substance, solution or composition in a medium where the latter is not or is only slightly soluble, or facilitating its accessibility to enveloped viruses. In accordance with the aims pursued by the present invention, the solubilizing agent is intended to enhance the solubility or the accessibility of the solvent with respect to the enveloped viruses present in the viral preparation of interest with the aim of enhancing the efficiency of the method according to the invention. Of course, the solvent and the solubilizing agent may be introduced individually into the viral preparation (the solubilizing agent before or after the solvent) or simultaneously. In particular, when the method of inactivation according to the invention is used on a viral preparation during purification, it may be advantageous to introduce the solubilizing agent right at the first stages of purification and then to introduce the solvent during the method according to the invention. Optionally, subsequent purification steps will be able to improve the purity of the viral preparation, in particular by removing from the final product the solvent and, where appropriate, the solubilizing agent used.

Although the choice of the solubilizing agent is not limited, there may be mentioned in particular the polyoxyethylene derivatives of fatty acids or of their esters. The preferred solubilizing agents include Tween (in particular Tween® 20 or 80), Triton (in particular X-100), PEG (in particular PEG 400), sodium cholate, sodium deoxycholate, octyl β-D-glucopyranoside and N-dodecyl-N,N-dimethyl-2-ammonio-1-ethane sulphonate. Tween® 80 is most preferred. The combination TNBP and Tween® 80 is preferred in the context of the invention.

In the case where this embodiment is selected, the final concentration of solubilizing agent to be used may vary in a wide range. As a guide, is may be between 0.001% and 10%, in particular between 0.01% and 5% and preferably between 0.1% and 2%. As regards Tween® 80, the optimum concentration is between 0.5% and 2%. The combinations TNBP 0.6% and Tween® 80 2% as well as TNBP 0.3% and Tween® 80 1% are particularly preferred.

Moreover, the method according to the invention may also be carried out in the presence of one or more other substances enhancing the efficacy of the solvent with respect to enveloped viruses, its stability or its solubility or reducing interfering activities capable of hampering the inactivation of the enveloped viruses and/or the infectivity of the non-enveloped viruses. In this regard, there may be mentioned in particular the anti-proteases. This embodiment is particularly appropriate for carrying out the method using Hecameg as solvent.

The temperature at which the method according to the invention is carried out is between −5 and +50° C. However, in order to ensure the infectivity of the non-enveloped viruses of the viral preparation, a temperature of between about +4° C. and +37° C., and more particularly between about +15° C. and +25° C., is preferred, room temperature being quite appropriate.

The method according to the invention is carried out at a pH of between about 5 and about 9. However, it is preferable to carry out the procedure at a pH of between 6.5 and 8.5 and preferably at a pH of about 8.5. Persons skilled in the art are capable of adjusting the pH using buffered solutions or by addition of bases or acids to respectively increase or reduce the pH according to the needs.

In the context of the method according to the invention, the time for the reaction between the solvent, optionally in the presence of the solubilizing agent, and the viral preparation, may vary as a function of different parameters (volume of the viral preparation, types of enveloped viruses, reaction temperature, and the like). The reaction time appropriate for the experimental conditions can be easily determined by persons skilled in the art with the aid of simple comparative tests. As a guide, the reaction time is between 15 mm and 24 h, advantageously between 30 mm and 12 h and preferably between 1 h and 5 h. Extending the reaction time may be considered for particularly large volumes of viral preparation or a low reaction temperature. Moreover, in the case where a reduction in the reaction time is sought, persons skilled in the art are capable of determining the appropriate rise in the reaction temperature.

Preferably, the method according to the invention is carried out with stirring. Indeed, it is observed that the non-enveloped virus yield is increased under these conditions. Although the choice of stirring speed is very wide, it is preferable to carry out the operation at a stirring speed between about 50 and about 5000 revolutions/min, advantageously between about 100 and about 2000 revolutions/min and preferably between about 150 and about 500 revolutions/min. It is possible to use a magnetic stirrer or any other appropriate apparatus (for example a tank provided with propeller or paddle mixers).

Finally, it is preferable to carry out the method according to the invention under conductivity conditions between about 5 and about 500 mS/cm. advantageously between about 10 and about 200 mS/cm and preferably between about 10 and about 100 mS/cm. These conditions are advantageous for preserving the infectivity of the non-enveloped viruses of interest.

Moreover, the method according to the invention may apply to one or more types of enveloped viruses derived from a variety of sources, such as for example the raw material, the biological material, the environment or the operators involved in the preparation and the purification of the non-enveloped viruses of interest. Preferably, the method of the invention is particularly useful for inactivating the enveloped viruses which are pathogenic for humans. Among these, there may be mentioned the hepatitis viruses, the retroviruses, the Epstein-Barr virus, the cytomegaloviruses, the herpesviruses, the rhabdoviruses, the myxoviruses, the paramyxoviruses, the orthomyxoviruses, the arenaviruses, the coronaviruses and foreign agents. In the context of the present invention, the method of the invention applies more particularly to the retroviruses and to the hepatitis viruses. The validation of the method according to the invention may be carried out by introducing into a viral preparation of—interest a known quantity of enveloped viruses which are particularly stable to inactivation, such as for example BVD (bovine viral diarrhoea), PRV (pseudorabies virus), VSV (vesicular stomatitis virus), retroviruses or HSV (herpes simplex virus). The method of inactivation of the invention is validated when the concentration and/or the infectivity of the "test" enveloped viruses is significantly reduced, that is to say by at least 4 log units. In addition, since the method of inactivation of the invention is integrated in an overall method of preparing a viral preparation, it is also possible to envisage an overall validation which makes it possible to quantify the inactivation resulting from all the steps of the method of preparation. An example of validation of the inactivation step is provided below.

The method of inactivation according to the invention applies to a viral preparation comprising non-enveloped viruses of interest. There may be advantageously mentioned the adenoviruses, indo-viruses, papovaviruses, rotaviruses and parvoviruses. Among these, the AAVs (adenovirus-associated viruses of the parvovirus family) and the adenoviruses are preferred. The method of the invention is most particularly suitable for the preparation of replication-defective recombinant adenoviruses. "Recombinant" refers to the presence of one or more genes of interest placed under the control of elements appropriate for its (their) expression in a host cell. "Replication-defective" means incapable of autonomous replication in a host cell (in the absence of complementation.

Advantageously, the gene of interest encodes an antisense RNA, a ribozyme, or a polypeptide of interest. It may be derived from a eukaryotic organism, a prokaryote, a parasite or a virus other than an adenovirus. It may be isolated by any conventional technique in the prior art (by cloning, PCR, chemical synthesis and the like). It may be of the genomic type (comprising all or part of the set of introns), of the complementary DNA type (cDNA, free of intron) or of the mixed type (minigene). Moreover, the polypeptide which it encodes may be (i) intracellular, (ii) incorporated into the membrane of the host cell or (iii) secreted. This may be a polypeptide as found in nature (native), a portion thereof (truncated), a mutant exhibiting in particular enhanced or modified biological properties or a chimeric polypeptide obtained from the fusion of sequences of diverse origins.

Among the polypeptides of interest which can be used, there may be mentioned more particularly chemokines (MIP-1α, MIP-1β, RANTES, DC-CK1, MDC, MCP1 (monocyte chemoattraction protein), IP10 and the like), cytokines (α, β, or γ-interferon, interleukin (IL), in particular IL-2, IL-6, IL-10 or IL-12, colony-stimulating factor (GM-CSF, C-CSF, M-CSF) and the like), cellular receptors (in particular recognized by the HIV virus), receptor ligands, coagulation factors (factor VIII, factor IX, thrombin, protein C), growth factors, proangiogenic factors (FGF for Fibroblast Growth Factor, VEGF for Vascular Endothelial Growth Factor, SH/HGF for scatter factor/Hepatocyte growth factor, TGF for transforming growth factor, TNF for tumour necrosis factor, angiopoietin), enzymes (urease, renin, metalloproteinase, nitric oxide synthetase NOS, SOD, catalase, lecithin cholesterol, acyl transferase LCAT, and the like), enzyme inhibitors (α1-antitrypsin, antithrombin III, viral protease inhibitor, PAI-1 for plasminogen activator inhibitor), antigens of the major histocompatibility complex class I or II or polypeptides acting on the expression of the corresponding genes, antigens (or antigenic peptides) capable of generating an immune response, polypeptides capable of inhibiting a viral, bacterial or parasitic infection or its development, polypeptides with antitumour effect (products of expression of tumour suppressor genes, tumour-associated antigens, and the like), polypeptides acting positively or negatively on apoptosis (Bax, Bc12, Bc1X, and the like), cytostatic agents (p21, p16, Rb), complete or partial immunoglobulins (Fab, ScFv, and the like), toxins, immunotoxins, apolipoproteins (ApoAI, ApoAIV, ApoE, and the like), cytotoxic products, antiangiogenic factors (angiostatin, endostatin, PF-4, and the like), markers (β-galactosidase, luciferase, green fluorescent protein) or any other polypeptide having a therapeutic effect for the condition targeted.

More precisely, with the aim of treating a hereditary dysfunction, there will be used a functional copy of the defective gene, for example a gene encoding factor VIII or IX in the case of haemophilia A or B, dystrophin (or minidystrophin) in the case of Duchenne and Becker myopathies, insulin in the case of diabetes, CFTR (Cystsic Fibrosis Transmembrane Conductance Regulator) protein in the case of cystic fibrosis. As regards inhibiting the onset or the progression of tumours or cancers, there will preferably be used a gene of interest encoding an antisense RNA, a ribozyme, a cytotoxic product (herpes simplex virus 1 thymidine kinase (TK-HSV-1), ricin, cholera or diphtheria toxin, product of the yeast genes FCY1 and FURI encoding uracyl phosphoribosyl transferase and cytosine deaminase, and the like), an immunoglobulin, an inhibitor of cell division or of the transduction signals, a product of expression of a tumour suppressor gene (p53, Rb, p73, DCC, and the like), a polypeptide stimulating the immune system, a tumour-associated antigen (MUC-1, BRCA-1, papillomavirus early or late antigens), optionally in combination with a cytokine gene. Finally, in the case of an anti-HIV therapy, it is possible to use a gene encoding an immunoprotective polypeptide, an antigenic epitope, an antibody (2F5; Buchacher et al., 1992, Vaccines 92, 191-195), the extracellular domain of the CD4 receptor (sCD4; Traunecker et al, 1988, Nature 331, 84-86) an immuno-adhesin (for example a CD4-immunoglobulin IgG hybrid; Capon et al., 1989, Nature 337, 525-531; Byrn et al., 1990, Nature 344, 667-670), an immunotoxin (for example fusion of the antibody 2F5 or of the immunoadhesin CD4-2F5 with angiogenin; Kurachi et al., 1985, Biochemistry 24, 5494-5499), a transdominant variant (EP 0614980, WO95/16780), a cytotoxic product such as one of those mentioned above or an IFNα or β.

One of the genes of interest may also be a selectable gene allowing the transfected or transduced cells to be selected or identified. There may be mentioned the neo genes (encoding neomycin phosphotransferase) conferring resistance to the antibiotic G418, dhfr (Dihydrofolate Reductase) gene, CAT (Chloramphenicol Acetyl transferase) gene, pac (Puromycin Acetyl-Transferase) gene or gpt (Xanthine Guanine Phosphoribosyl Transferase) gene. In general, the selectable genes are known to persons skilled in the art.

Generally, the gene(s) of interest are placed under the control of regulatory elements allowing their expression in the host cell or organism. They are the set of genetic elements allowing the transcription of a gene of interest into RNA and the translation of an mRNA into the polypeptide. Among these, the promoter is of particular importance. It may be isolated from any gene of eukaryotic or even viral origin and may be constitutive or regulatable. Alternatively, it may be the natural promoter of the gene in question. Moreover, it may be modified so as to enhance the promoter activity, suppress a region inhibiting transcription, render a constitutive promoter regulatable or vice versa, introduce a restriction site, and the like. There may be mentioned, by way of examples, the eukaryotic promoters of the PGK (Phospho Glycerate Kinase), MT (metallothionein; Mc Ivor et al., 1987, Mol. Cell. Biol. 7, 838-848), or SRα (Takebe et al., 1988, Mol. Cell. Biol. 8, 466-472) genes, the SV4O virus (Simian Virus) early promoter, the RSV (Rous Sarcoma Virus) LTR, the TK-HSV-1 promoter, the CMV virus (Cytomegalovirus) early promoter and the adenoviral promoters E1A and MLP.

A promoter in use in the present invention may also stimulate expression in a tumour or cancer cell. There may be mentioned in particular the promoters of the MUC-1 gene which is overexpressed in breast and prostate cancers (Chen et al., 1995, J. Clin. Invest. 96, 2775-2782) of the CEA (for carcinoma embryonic antigen) gene which is overexpressed in colon cancers (Schrewe et al., 1990, Mol. Cell. Biol. 10, 2738-2748), of the tyrosinose gene which is overexpressed in melanomas (Vile et al., 1993, Cancer Res. 53, 3860-3864), the ERB-2 gene which is overexpressed in cancers of the breast and of the pancreas (Harris et al., 1994 Gene Therapy 1, 170-175) and the α-fetoprotein gene which is overexpressed in liver cancers (Kanai et al., 1997, Cancer Res. 57 461-465). A promoter which is capable of being regulated by hormonal or exogenous substances (steroid hormones, tetracycline, and the like) may also be envisaged (Saez et al., 1997, Current Opinion in Biotechnology 8, 608-616).

It is also possible to use a tissue-specific promoter. Purely by way of illustration, there may be mentioned the liver-specific promoters (of the α-1-antitrypsin, albumin, FIX or ApoAI genes, and the like), the lung-specific promoters (of the surfactant or CFTR genes), the lymphocyte-specific promoters (immunoglobulin) and the muscle-specific promoters (β-actin, Tabin et al., 1982, Mol. Cell Biol. 2, 426-436; SM22; Moessler et al., 1996, Development 122, 2415-2425 and Desmin, Li et al., 1989, Gene 78, 243-254).

Moreover, the regulatory elements may, in addition, include additional elements enhancing the expression or the maintenance in the host Cell of the gene of interest (replication origin, elements for integration into the cellular genome, intron sequences, poly A sequences for termination of transcription, tripartite leaders, and the like). These elements are known to a person skilled in the art. In addition, the gene of interest may also comprise, upstream of the coding region, a sequence encoding a signal peptide allowing its secretion from the host cell. The signal peptide may be that of the gene in question or may be heterologous (derived from any gene which is secreted or synthetic).

The gene of interest may be inserted at any site in the genome of the non-enveloped virus, advantageously as a replacement for the EI or E3 region when an adenovirus is involved. When the recombinant adenoviral vector comprises several genes of interest, these may be placed under the control of the same genetic elements (polycistronic cassette using an internal site for initiation of translation of the IRES type for reinitiating the translation of the second cistron) or of independent elements. In this case, they may be inserted into the same viral region (for example as a replacement for EI) or into different regions (for example as a replacement for EI and for another deleted region).

A defective virus may be obtained by a nonfunctional mutation or by a total or partial deletion of a region which is essential for viral replication. There will preferably be used an adenoviral vector lacking all or part of at least one region which is essential for replication, selected from the EI, E2, E4 and L1 to L5 regions, so as to avoid its propagation in the host organism or the environment. A deletion of most of the EI region is preferred. Advantageously, it extends from nucleotides (nt) 454 to 3328, but may also cover additional sequences in 5' and/or in 3', on the condition that it does not interfere with the encapsidation function. Preferably, the pIX gene is not included in the deletion of EI. A deletion extending up to nt 3510 meets these criteria.

In addition, the deletion of EI may be combined with other modification(s) affecting in particular the E2, E4, L1, L2, L3, L4 and/or L5 regions, insofar as the defective essential functions are complemented in trans by means of a complementation line and/or a helper virus. In this regard, it is possible to use second-generation vectors which are defective for the EI and E4 or EI and E2 functions (see for example international applications WO94/28152 and WO97/04119). To illustrate this embodiment, there may be mentioned a vector combining a deletion in the EI region and a heat-sensitive mutation affecting the DBP (for DNA Binding Protein) gene of the E2A region (Ensinger. et al., 1972, J. Virol, 10, 328-339) or a deletion of the latter. As regards the E4 region, it may be deleted completely or in part. A partial deletion of the E4 region, with the exception of the sequences encoding the open reading frames (ORF) 3 and/or 6/7, is advantageous since it does not require complementation of the E4 function (Ketner et al., 1989, Nucleic Acids Res. 17, 3037-3048). Another alternative consists in maintaining in the adenoviral skeleton the sequences of E4 encoding the ORFs 3 and 4 or the ORFs 3, 6 and 7, which have a beneficial effect on the expression of the gene of interest.

With the aim of increasing the cloning capacities, the recombinant adenoviral vector may, in addition, lack all or part of the non-essential E3 region. According to this alternative, it may be advantageous to nevertheless conserve the E3 sequences encoding the polypeptides allowing escape from the host immune system, in particular the glycoprotein gp19k (Gooding et al., 1990, Critical Review of Immunology 10, 53-71). According to another alternative, it is possible to use a minimal adenoviral vector retaining essentially the 5' and 3' ITRs (Inverted Terminal Repeat) and the encapsidation region and defective for all the viral functions.

Moreover, the region of the adenoviral vector may be varied both from the point of the view of the species and of the serotype. It may be derived from the genome of a human or animal (canine, avian, bovine, murine, ovine, porcine, simian, and the like) adenovirus or a hybrid comprising fragments of adenoviral genome of at least two different origins. There may be mentioned more particularly the canine adenoviruses CAV-1 and CAV-2, the avian adenovirus DAV or the bovine adenovirus Bad (in particular type 3) (Zakharchuk et al., Arch. Viral., 1993, 128: 171-176; Spibey and Cavanagh, J. Gen. Virol., 1989, 70: 165-172; Jouvenne et al., Gene, 1987, 60: 21-28; Mittal et al., J. Gen. Virol., 1995, 76: 93-102). However, an adenoviral vector of human origin, derived from a serotype C, in particular type 2 or 5, adenovirus will be preferred.

The subject of the invention is also a method of preparing a viral preparation predominantly containing non-enveloped viruses, the said method comprising at least one step for inactivating enveloped viruses according to the method of the invention.

Advantageously, the method of preparation according to the invention comprises at least:

(a) one step for producing the viral preparation in an appropriate cell line, (b) one step for harvesting the viral preparation produced in step (a) from the producing cell line and/or from the culture supernatant, (c) optionally, one step for breaking the cells of the producing cell line, (d) optionally, one clarification step,
(e) one step for inactivating enveloped viruses as described above, and
(f) optionally, one purification step.

Of course, the order of the steps may vary, in particular as regards the inactivation step (e), which may be placed immediately after the harvesting of the viruses (step b), after the optional steps c) or d) or may be included in the purification step f).

As indicated above, step (a) may result from the transfection of the genome of the non-enveloped virus of interest into an appropriate cell line. The viral DNA introduced may be the viral genome, optionally constructed in a bacterium (WO96/17070), in a yeast (WO95/03400) or in a cell. The construction is carried out by molecular biology or intermolecular homologous recombination techniques which are conventional in the prior art. The DNA may also be introduced into, the cell line in the form of fragments comprising a portion of the viral genome and having a region of homology allowing the complete genome to be reconstituted by recombination between the homologous sequences carried by each of the fragments (Graham and Prevect, 1991, Methods in Molecular Biology, Vol 7, p 109-128; Ed Murey, The Human Press Inc.). Another alternative consists in infecting the cell line with a viral prestock. The conditions for infection may be defined by persons skilled in the art. By way of illustration, the cells are infected with the non-enveloped virus at a defined multiplicity of infection (MOI) (about 1 to 10 in the case of a defective adenovirus).

After transfection or infection, the culture is continued, preferably at 37° C., for a time which is sufficiently long to allow the amplification of the viruses. Depending on the quantity of virus to be produced, this step is carried out in culture dishes, in a fermenter or in any other appropriate culture system. Generally, the harvesting of the non-enveloped viruses is carried out between 24 h and 1 week post-infection or -transfection. The harvesting time may be determined by several criteria: the optimum viral titre, observation of a cytopathy (rounding of the producing cells) and/or reduction in the consumption of oxygen. Harvesting at 48 h or 72 h is preferred. The viruses are collected either from the producing cells or from the culture supernatant or from the cells and supernatant combined.

In the first case, the producing cells are harvested. It is preferable to carry out a step of breaking the cells, generally after resuspending the cellular biomass, in order to release, the viruses produced intracellularly. All conventional means may be used in the context of the invention, in particular chemical and/or mechanical means. It is possible to carry out, for example, freeze-thaw cycles which make the cell membranes fragile, an enzymatic lysis (use of enzymes which degrade the cell membranes) or chemical lysis (use of detergent, pH shock, osmotic shock and the like). The mechanical means may result from ultrasound (sonication), attrition (DynoMill glass beads, BeadMill), pressure and shear forces (French Press high-pressure homogenizer), microfluids (Microfluidics, Newton, Mass.) or the mechanical action of two rollers generating hydraulic and mechanical shear forces (Silverson homogenizer).

When the viral preparation is harvested directly from the culture medium, it is not necessary to carry out the breaking step, it being possible for the culture supernatant to be directly clarified in order to remove the cellular debris, for example by low-speed centrifugation or cascade filtration. In this case, the culture may be continued for a longer period in order to ensure a maximum yield of virus.

According to a third option, the supernatant and the cells may be harvested. In this case, it is advisable to carry out the breaking step in order to release the intracellular viruses, and the clarification step.

The aim of the clarification step is to remove the insoluble matter (cellular debris, flocculates of micromolecules, and the like). It can be carried out by any conventional filtration technique (depth filtration, tangential microfiltration and the like) and centrifugation (continuous and the like). It may be judicious, in particular when the viral preparation is highly concentrated, to remove most of the insoluble matter, first by centrifugation, and then to continue the clarification by depth filtration. Many filters can be used in the context of the present invention on condition, however, that they have a porosity which makes it possible to allow the non-enveped virus of interest to pass through, and to retain the insoluble matter. It should be stated that adenoviruses have a size of about 0.07 to 0.1 μm, which requires the use of filters of higher porosity. Moreover, the filters may be made of synthetic material (nylon), organic material (cellulose) or non-organic material (zirconium). According to an advantageous embodiment, successive filtrations are carried out on filters of decreasing porosity, for example first on a filter having a porosity of 8 μm (Sartorius 5591301 P5-00), then on a filter having a porosity of 5 μm (Sartorius 5591342P5-00), then on a filter having a porosity of between 3 and 0.8 μm (Sartorius, Sartoclean CA capsule 5621304E9-00-A), and then on a filter having a porosity of between 0.8 and 0.65 μm (Sartorius, Sartoclean CA capsule 5621305G9-00-A). According to another variant, the filtration may be carried out by tangential microfiltration on flat membranes or hollow fibres having a porosity greater than the size of the adenovirus. In this regard, the Durapore (Millipore) and Omega (Pall) membranes may be used.

The purification step may be carried out by previous conventional techniques, for example by ultracentrifugation (on a caesium chloride gradient and the like) or chromatography.

According to an advantageous embodiment, the purification step of the method of preparation according to the invention comprises a chromatographic step, in particular by ion exchange. Optionally, it may be combined with a different type of chromatography, in particular by gel filtration in order to perfect the purification of the non-enveloped viruses. The two chromatographies may be carried out in any order, but it is nevertheless preferable to first carry out the ion-exchange chromatography, and then the gel filtration chromatography.

For the ion-exchange chromatography, various types of supports may be used, such as the supports based on cellulose, agarose (Sepharose or Macro-Prep gels), dextran (Sephadex gels), acrylamide (Sephacryl, Trisacryl gels), silica (TSK, SW gels), poly(styrene-divinylbenzene) (Source or Poros gels), ethylene glycol-methacrylate copolymers (Toyopearl HW, TSK, PW, fractogel EMD gels) or mixtures, in particular of agarose and dextran (Superdex gel). The supports approved for human or veterinary use by the competent American authorities (FDA for food and drug administration) or the European Union agencies will be more particularly selected. In addition, the support selected must be bonded, preferably by covalent bonding, to one or more types of group capable of ineteracting with the non-enveloped virus to be purified (the support is said to be functionalized). A group would be preferred which allows an exchange of anions, in particular consisting of ternary or quaternary amine. Among the supports functionalized with ternary amines, there may be mentioned the Fractogel- DEAE (diethylaminoethyl), Fractogel-DMAE (dimethylaminoethyl) and Toyopearl-DEAE resins. Among the supports functionalized with quaternary amines, there may be mentioned the Source Q, Mono Q, Q Sepharose, Poros HQ and QE resins, Streamline QXL (French application n° 99 02167) and the resins of the Fractogel-TMAE and Toyopearl super Q type. The Poros P1 resin is an appropriate example of a support functionalized with polyethylenimine. The Fractogel-DEAE support is preferred in the context of the present invention. The column is initially equilibrated under saline conditions allowing the attachment of the non-enveloped viruses of interest to the positively charged functional groups. Advantageously, a buffer comprising NaCl at about 250 mM final is used. However, the chromatographic conditions may of course adjusted as a function of different parameters, in particular the volume of the column, the support chosen, the virus chosen and the viral concentration. The elution of the virus retained on the amine groups is carried out by gradually increasing the saline concentration, preferably to a final concentration of 300 to 400 mM NaCl and, most preferably, between 300 and 350 mM NaCl and the fractions comprising the non-enveloped virus of interest may be determined by any prior art technical means (spectrophotometric measurement of the absorbance at 260 and 280 nm, visualization of viral genomes or peptides, and the like). It is also possible to connect the column to a detector provided with a filter for the on-line detection of the viral fractions. It should be stated that the viral fraction (composed of DNA and of proteins) has a characteristic absorbance at 260 and 280 nm whereas the protein contaminants are detected only at 280 nm and the free nucleic acids at 260 nm.

As regards the gel fitration chromatography, the virus is purified on a support having a bead diameter of between 3 and 160 μm, advantageously between 5 and 105 μm and preferably between 10 and 80 μm. Preferably, the support has a porosity close to the size of the virus so that the latter does not penetrate inside the beads. By contrast, all the molecules which are smaller in size will penetrate into the beads and be retarded. Various types of supports may be used, such as the matrices based on agarose (Sepharose), dextran (Sephadex gels), acrylamide (Sephacryl and Trisacryl gels), silica (TSK and SW gels), ethylene glycol-methacrylate copolymers (Toyopearl HW, TSK and PW gels), and mixtures, in particular of agarose and dextran (Superdex gel). The supports mentioned are preferably used without functionalizing groups. The supports which are particularly appropriate for carrying out the method of preparation according to the invention are the following:

- allyl dextran-methylene bisacrylamide matrices (Sephacryl S300 HR having a bead diameter of between 25 and 75 μm, Sephacryl S400 HR having a bead diameter of between 25 and 75 μm, Sephacryl S500 HR having a bead diameter of between 25 and 75 μm and Sephacryl S1000 SF having a bead diameter of between 40 and 105 μm; Pharmacia),
- ethylene glycol-methacrylate matrices (Toyopearl HW 55, Toyopearl HW 65 and Toyopearl HW 75 having a bead diameter varying from 20 to 60 pm; Tosohaas),
- N-acrylamine hydroxypropanediol matrices (Triacryl having a bead diameter of between 80 and 160 μm; Biosepra), and
- agarose matrix (Macro-Prep SE having a bead diameter of between 20 and 80 μm; Biorad).

As a guide, the Toyopearl HW65F or HW6SS (porosity 1000 Å) or Sephacryl S400HR type support is preferred. The column is equilibrated in a buffer having saline conditions and a pH which limits the hydrophobic interactions between the support and the virus. Advantageously, a 50 mM Tris-HCl buffer containing 2 mM $MgCl_2$ and 2% sucrose, at pH 8.5, is used. The non-enveloped viruses of interest pass through the beads without being retained and come out before the contaminants of lower molecular weight. The fractions containing them may be determined by the usual techniques (absorbance at 260 and 280 nm, electrophoresis or PCR techniques, and the like). It will be noted that one advantage of the method of preparation according to the invention consists in the removal, during this step (f), of the solvent and of the solubilizing agent in use in the method of inactivation according to the invention. According to an optional embodiment, the viral fractions obtained after the purification step may be combined and optionally concentrated using the usual techniques. There may be mentioned tangential ultrafiltration and diafiltration. The BioMax PES (Millipore reference PXB300C50) and PLCMK (Millipore reference PXC300C50 or PXBO1MC50) cartridges are most particularly suitable.

In addition, the method of preparation according to the invention may comprise additional steps and in particular a step for degrading the nucleic acids (mainly of cellular origin) present in large quantities after breaking the cells. To this effect, all the non-specific restriction enzymes of the endo- or exonuclease type may be used. However, the preferred method consists of a treatment with benzonase. As a guide, about 5 to 50 U/ml of benzonase are used, but the optimum conditions may be adjusted by persons skilled in the art according to the volume to be treated and the viscosity of the viral preparation. The action of the benzonase may be assessed by the reduction in the concentration of nucleic acids by applying any methodology disclosed in the literature. Although the steps can be interchanged, it is preferable to carry out the said benzonase treatment step between the breaking (c) and clarification (d) steps of the said method of preparation. Another alternative consists in carrying out the benzonase treatment step and the inactivation step simultaneously after breaking and clarification steps. In addition, the benzonase can be used optionally in the presence of β-cyclodextrin. The latter helps to precipitate lipids and may be added at a final concentration of 0.1 to 10% and, in particular, 1.5%.

The method of preparation according to the invention may also comprise a sterilizing filtration step, the said sterilizing filtration step being preferably carried out after step (f) of the said method of preparation. Use will be advantageously made of 0.22 gin filters having a surface area appropriate for the volume to be treated. There may be mentioned, for example, the filtration units of the Minisart (Sartorius, reference SM16534), Sartolab P20 (Sartorius, reference 18053D), Millex GF (Millipore, reference SLGO25BS), Millex GV (Millipore, reference SLGVO25BS), Millex GP (Millipore, reference SLGPR25LS) or Spirale Cap (Version Super CQS 92 HS or HP; Gelman Sciences), Criticap 50 (12995, Gelman Sciences) or Millipak (Milliporel ref. MPGLO4SK2 or MPGLO2SH2) type. Next, the filtrate may be packaged in doses adjusted to a given concentration.

The quality, that is to say the degree of purity of the viral preparation, may be monitored throughout the method of preparation according to the invention by determining the residual concentration of the contaminants and the functionality of the non-enveloped virus of interest. In the first case, and this being the preferred embodiment, the disappearance of Tween® 80 (or polysorbate 80) after step (f) may be assessed by the method recommended in the European Pharmacopoeia (1997, p. 1372-1373) with the aid of potassium thiocyanate and chloroform. The quantity of TNBP present in the viral preparation may be titrated by the gas chromatography technique as disclosed in the Horowitz et al. (1985, Transfusion 25, 516-522). The residual concentration of the proteins may be measured by any technique for assaying proteins. A suitable technique is that of BCA (bicinchoninic assay) (kit Micro BCA Protein Assay Reagent Kit; Pierce ref 23235). As regards the viral active ingredient, the number of complete particles is determined by the spectrometry at a wavelength of 260 nm in the presence of SDS (see Shabram et al., 1997, Human Gene Therapy 8, 453-465). The functionality of the non-enveloped virus is generally determined by its infectious capacity, for example by titrating the number of infectious units (see Lusky et al., 1998, J. Virol. 72, 2022-2032). In the case of a recombinant virus, it is also possible to evaluate the expression of the recombinant gene, after infecting the target cell, by fluorescence, immunological methods (ELISA, RIA and the like), immunoenzymatic methods (Western and the like), staining techniques or luminescence, and the like.

The method of preparation according to the invention applies to non-enveloped viruses such as those cited above and, more particularly, to adenoviruses. Preferably, the latter exhibit the characteristics defined above.

The choice of the different cell lines appropriate for carrying out the method according to the invention is wide and within the capability of persons skilled in the art. A line suitable for the non-enveloped virus selected will be chosen. In the case of the preferred embodiment (replication-defective recombinant adenovirus), a complementation line suitable for the deficiencies of the adenovirus such as those described in the literature will be used. This is advantageously a line complementing the E1 function, such as for example the 293 line obtained from human embryonic kidney cells and which comprises, integrated into its genome, the 5' end of the Ad5 genome (Graham et al., 1977, J. Gen. Viral. 36, 59-72). Other E1 complementing lines are also available (Imler et al., 1996, Gene Therapy 3, 75-84; Fallaux et al., 1996, Human Gene Therapy 7, 215-222; Fallaux et al., 1998, Human Gene Therapy 9, 1909-1917). When the deficiencies of the virus also apply to the E2 or E4 regions, it is possible to use the complementation lines described in Brough et al. (1992, Virology 190, 624), Wang et al. (1995, Gene Therapy 2, 775-783), Yeh et al. (1996, J. Viral 70, 559-565), Kougliak and Graham (1996, Human Gene Therapy 6, 1575-1586) and Lusky et al., (1998, J. Viral, 72, 2022-2032) and in international applications WO94/28152 and WO97/04119. Another alternative is based on the use of an additional viral element, designated "helper virus", to complement, at least in part, the defective functions of the non-enveloped virus of interest. The helper viruses of the prior art consist of a viral genome, optionally deleted for an essential region for which the virus of interest does not require complementation or which is provided by the line. In general, a complementation line may be generated by transfection of the viral sequences, restoring the defective function(s) of the virus, placed under the control of the elements necessary for their expression in an appropriate cell line. In this regard, it may be derived from an established cell line of human or animal origin and, preferably, acceptable from a pharmaceutical point of view (capable of being used for the production, on an industrial scale, of products intended for human use and not having any known pathogenic character). There may be mentioned, inter alia, the KB, HeLa, Vera (ATCC CCL-81), BHK (ATCC CCL-10), A 549 (ATCC CCL-185), MRC5 (ATCC CCL-171), WI-38 (ATCC CCL-75), CEO, MDCK and MDBK cells. An appropriate line in the context of the present invention may also be derived from a primary cell and in particular from retinal or kidney cells collected from a human embryo. Use is preferably made of a line derived from a human embryonic kidney cell, from a retinal cell (in particular from human embryonic retina HER) or from a human carcinoma (A549).

The present invention also relates to a viral preparation obtained according to the method of preparation according to the invention as well as a eukaryotic cell infected with a viral preparation according to the invention. This is preferably a mammalian, and in particular human, cell. It may be a primary or tumour cell and of any origin, in particular of haematopoietic (totipotent stem cell, leukocyte, lymphocyte, monocyte or macrophage and the like), muscle (satellite cell, myocyte, myoblast, smooth muscle and the like), cardiac, pulmonary, tracheal, hepatic, epithelial or fibroblast origin. It should stated that the preparation of the invention is distinguishable from those of the prior art in that it is essentially free of infectious enveloped viruses.

The present invention also relates to a composition comprising a viral preparation or a host cell according to the invention. As a reminder, the said viral preparation may comprise one or more non-enveloped viruses of interest prepared according to the method of the invention. These may be of the same family (adenoviruses carrying a different recombinant gene) or not. The said composition is preferably a pharmaceutical composition containing at least one pharmaceutically acceptable vehicle.

A composition according to the invention may be manufactured in a conventional manner for administration by the local, parenteral or digestive route. The routes of administration which may be envisaged are many. There may be mentioned, for example, the intragastric, subcutaneous, intracardial, intramuscular, intravenous, intra-arterial, intravascular, intraperitoneal, intratumour, intranasal, intrapulmonary or intratracheal route. For the latter three embodiments, administration by aerosol or instillation is advantageous. The administration may take place in a single dose or in a dose repeated once or several times after a certain time interval. The route of administration and the appropriate virus doses vary according to various parameters, for example the individual, the pathology, the gene of interest to be transferred, the route of administration. As a guide, the preparations based on adenoviral particles may be formulated in the form of doses of between $10^4$ and $10^{14}$ pfu (plaque forming units), advantageously $10^5$ and $10^{13}$ pfu and, preferably, $10^6$ and $10^{12}$ pfu.

The formulation may also include a pharmaceutically acceptable diluent, adjuvant or excipient, as well as solubilizing, stabilizing and preserving agents. A preferred composition is in an injectable form. It may be formulated in an aqueous, saline (phosphate, monosodium, disodium, magnesium, potassium and the like) or isotonic solution. The formulation buffer described in international application WO98/02522 is most particularly suitable. It may be presented in a single dose or in a multidose in liquid form or in a dry form (powder, lyophilisate and the like) capable of being reconstituted immediately before use with an appropriate diluent.

A composition according to the invention is more particularly intended for the preventive or curative treatment of diseases by gene therapy (including immunotherapy) and is intended more particularly for proliferative diseases (cancers, tumours, dysplasia, and the like), for infectious diseases and in particular viral diseases (induced by the hepatitis B or C viruses, HIV, herpes, retroviruses, and the like), for genetic diseases (cystic fibrosis, dystrophin, haemophilia, diabetes, and the like) and for cardiovascular diseases (restenosis, ischaemia, dyslipaemia, and the like).

The present invention also relates to the therapeutic or prophylactic use of a viral preparation of a host cell, of a composition or of a pharmaceutical composition according to the invention, for the preparation of a medicament intended for the transfer and the expression of the gene of interest in a cell or a host organism. The medicament is more particularly intended for the treatment of diseases by gene therapy. According to a first possibility, it may be administered directly in vivo (for example by intravenous injection, into an accessible tumour, into the lungs by aerosol, into the vascular system by means of an appropriate probe, and the like). It is also possible to adopt the ex vivo approach, which consists in removing cells from the patient (bone marrow stem cells, peripheral blood lymphocytes, muscle cells, and the like), transfecting or infecting them in vitro according to prior art techniques and readministering them to the patient after an optional amplification step. The prevention and treatment of many pathological conditions may be envisaged. A preferred use consists in treating or preventing cancers, tumours and diseases resulting from an undesirable cell proliferation. Among the applications which may be envisaged, there may be mentioned cancers of the breast, of the uterus (in particular those induced by the papilloma viruses), of the prostate, of the lungs, of the bladder, of the liver, of the colon, of the pancreas, of the stomach, of the oesophagus, of the larynx, of the central nervous system and of the blood (lymphomas, leukaemia, and the like). It is also useful in the case of cardiovascular diseases, for example to inhibit or delay the proliferation of the smooth muscle cells of the vascular wall (restenosis). Finally, as regards infectious diseases, the application to AIDS may be envisaged.

The invention also extends to a method for the treatment of diseases by gene therapy, characterized in that a viral preparation, a host cell or a composition according to the invention is administered to an organism or to a host cell requiring such a treatment.

EXAMPLES

The present invention is illustrated by the following examples, without being limited as a result.

The recombinant adenoviruses were constructed by the homologous recombination technique described in Chartier et al. (1996, J. Viral. 70, 4805-4810). The constructs used were produced according to general genetic engineering and molecular cloning techniques, which are detailed in Maniatis et al., (1989, Laboratory Manual, Cold Spring Harbor, Laboratory Press, Cold Spring Harbor, N.Y. or a more recent edition) or according to the manufacturer's recommendations when a commercial kit is used. The cloning steps use the E. coli 5K (hsdR, mcrA), DH5α [(recA1, endA1, hodRI7 (r-m-), supE44 thi-1, gyrA (nalr)] or NM522 (supE, thi, Δ(lac-proAB), Ahsd5, (r-m-) (F=proAB), lac1$^{q'}$ ZαM15) strain and the homologous recombination steps the E. coli BJ 5183 strain (Hanahan, 1983, J. Mol. Biol. 166, 557-580). In the case of the repair of the restriction sites, the technique used consists in a filling of the protruding 5' ends with the aid of the large fragment of E. coli DNA polymerase I (Klenow, Boehringer Mannheim). The DNA fragments are purified with the aid of the GeneCleanII® DNA purification kit (Bio101 Inc.). Moreover, the adenoviral genome fragments used in the different constructs are indicated precisely according to their position in the nucleotide sequence of the Ad5 genome as disclosed in the Genebank data bank under the reference M73260.

As regards the cell biology, the cells are transfected or transduced and cultured according to standard techniques well known to persons skilled in the art. Use is made of the cell lines 293 (ATCC CRL-1573), A549 E1+ (WO94/28152) and 293-E4ORF6+7 (Lusky et al., 1998, J. Virol. 72 2022-2032). It is understood that other cell lines may be used. The cells are maintained in culture at 37° C. in a humid atmosphere enriched with 5% $CO_2$ in DMEM medium (Dulbecco's Modified Eagle Medium, Gibco BRL) supplemented with 1 mM of glutamine, 1% of amino acids (Gibco BRL), 40 µg/l of gentamycin and 10% foetal calf serum (FCS, Gibco, BRL). The cells can also be produced in a cell culture reactor. The cells are transfected according to prior art techniques (calcium phosphate precipitation and the like). The infectious units (iu) or total viral particles titre is determined according to known techniques (Lusky et al., 1998, J. Virol. 72, 2022-2032).

The examples which follow were carried out with the aid of recombinant adenoviruses expressing a marker gene or a therapeutic gene. They are derived from the Ad5 serotype and have the following structure;

AdTG6297 is a first-generation adenoviral vector defective for the E1 function (deletion of nt 459 to 3328) and the E3 function (deletion of the Xbal fragment extending from nt 28592 to 30470) into whose genome is inserted, as a replacement for the E1 region, a cassette for expression of the marker gene encoding the GFP protein (for green fluorescent protein). The latter reacts to light excitation (485 nm) by emitting a fluorescent light whose intensity is measured by means of a filter (535 nm). More precisely, the cassette is composed of the CMV promoter followed by a chimeric intron, the sequence encoding the GFP protein and the SV4O virus polyA. The intron sequences are isolated from the plasmid pCI (Promega Carp, pCI mammalian expression vector E1731) and comprise the splice donor site of intron 1 of the human β-globin gene as well as the branching point and the splice acceptor site of the gene for a mouse immunoglobin. The viral particles are produced by transfection of the vector AdTG6297 into an EI complementation line (293 or A549 E1+) and amplified by successive passages on a permissive line (complementing E1).

The vector AdTG5643 is a second-generation vector deleted for the EI (nt 459 to 3328), E3 (nt 28592 to 30470) and E4 (nt 32994 to 34998) regions and expressing the human therapeutic CFTR gene. The expression cassette consists of the CMV early promoter, the CFTR cDNA and the poly A of the rabbit β-globin gene and is inserted in place of the deleted E1 sequences. The viral particles are produced by transfection of the vector AdTG5643 into an EI and E4 (293-E40RF6+7) complementation line and a viral stock constituted by successive passages on a permissive line (complementing E1 and E4). The vector AdTG13383 is a vector deleted for E1 (nt459 to 351.1) and E3 (nt28539 to 30470) regions and expressing the human therapeutic IL2 gene.

The expression cassette inserted in place of E1 sequences is constituted by CMV early promoter, the synthetic intron isolated from pCI plasmid, cDNA coding for human IL2 and poly A SV4O. Viral particles are produced by transfection of pTG13383 vector in a complementation line of E1 and viral stock is constituted by successive passages on a permissive line (complementing E1).

EXAMPLE 1

Preparation of Viruses from Complementation Cells

The A549-EI+ cells are cultured in culture dishes until a cell density of $2.5 \times 10^5$ cells/cm² is obtained, and are then infected with a prestock of AdTG6297 at the rate of an MOI of about 3. The infected cells are harvested at 72 h post-infection and centrifuged at low speed. The pellet is taken up in about 600 ml of serum-free culture medium. The viral preparation thus obtained corresponds to a volume of about 20 l.

The intracellular virus is released after breaking the cells subjected to the mechanical action, for 7 to 10 mm, of a Silverson homogenizer (L4R-Silverson) set at a rotating speed of 4200 revolutions/mm.

At this stage, the viral preparation is very viscous because of the release of the genomic DNA following the cell disruption. There is added to the viral preparation one volume of a buffer allowing optimum action of benzonase and consisting of 100 mM Tris, 4 mM $MgCl_2$, 4% sucrose, pH 8.5, to which the solubilizing agent Tween® 80 (Merck reference 8-22187-1000) has been added at a concentration of 2%. The mixture is stirred at room temperature before adding the benzonase in an amount of 50 U/ml (Merck reference 101697) and the reaction is allowed to continue for 1 to 2 h at room temperature and with stirring.

The viral preparation thus treated is then clarified by depth filtration in four successive stages. The first filtration is carried out through 8 μm filters (Sartorius 5591301P5-00), then on 5 μm filters (Sartorius 5591342P5-00), then on 3 to 0.8 μm filters (Sartoclean CA capsule 5621304E9-00-A) and followed by a fourth filtration through 0.8 to 0.65 μm filters (Sartoclean CA capsule 5621305G9-00-A).

The step of inactivating the enveloped viruses is carried out by the action of TNBP at a final concentration of 0.3%. To do this, the filtrate is diluted volume for volume in a 50 mM Tris buffer solution containing 2 mM $MgCl_2$, 2% sucrose, _350 mM NaCl and 0.6% TNBP (Aldrich 24-049-4), pH 8.5. It is also possible to add to the filtered viral preparation 9 volumes of a more concentrated buffer (50 mM Tris, 2 mM $MgCl_2$, 2% sucrose, 1.82 M NaCl and 3% TNBP, pH 8.5). It should be noted that the saline conditions used (250 mM NaCl final) correspond to the equilibration conditions for ion-exchange chromatography. The action of TNBP/Tween® 80 is allowed to continue, with stirring (500 rpm), at room temperature for 3 h or at 4° C. for 4 h.

For the ion-exchange chromatography step, the inactivated viral preparation is loaded onto a column containing fractogel EMD DEAE (Merck, reference 1,16883), previously equilibrated with 50 mM Tris buffer containing 2 mM $MgCl_2$, 2% sucrose, 250 mM NaCl, pH 8.5. After rinsing with the equilibration buffer, the constituents adsorbed onto the support are eluted with the preceding buffer in the presence of increasing salt concentrations (NaCl 300 mM, 350 mM, 400 mM and the like). A flow rate of 30 to 100 cm/h and preferably 50 cm/h is applied. The different eluted fractions are visualized by measuring the absorbance at 260 and 280 nm. Generally, the proteins (detected at 280 nm only) are eluted with the buffer containing 300 mM NaCl. The second elution peak (detected at 260 and 280 nm) contains the adenoviruses of interest which are eluted at a saline concentration of 350 mM. The column is regenerated in the presence of 1.5 M NaCl. The fractogel is regularly sanitized by passage of 0.5 N NaOH.

The viral fraction is then loaded onto a column containing Toyopearl gel HW-65F (Tosohaas, reference 43304 or 07465) or 65S (Tosohaas, reference 43354 or 07467) or Sephacryl S400HR (Pharmacia, reference 17-0609-10) previously equilibrated with 25 mM Tris buffer containing 2 mM $MgCl_2$, 2% sucrose, pH 8.5. Generally, the volume of viral preparation injected corresponds to 5 to 20% of the volume of the gel filtration column and the flow rate applied varies from 5 to 100 cm/h with a preference for 10 to 50 cm/h. The elution profile monitored by measurement of the absorbance at 280 nm shows that the adenovirus peak is the first peak obtained on leaving the column.

The next step consists in diafiltering the viral preparation in order to be able to package it in the formulation buffer. To this end, the viral fractions are assembled and the total viral particle and infectious unit titre is measured on one aliquot. If the viral titre is sufficient, the viruses are diluted in the formulation buffer, subjected to a sterilizing filtration on a 0.22 μm filter (Sartolab P20, sartorius reference 18053D) and divided into doses. If the titre is too low, the viral preparation may be previously concentrated by tangential ultrafiltration and/or diafiltration with the aid, for example, of the BioMax PES (Millipore reference PXB300C50) and PLCMK (Millipore reference PXC300C50) cartridges.

In a representative experiment carried out using a viral preparation of AdTG6297 expressing the GFP marker, the result in viral titre is the following:

| Steps | Total iu × 1011 | Yield (%) |
|---|---|---|
| Start | 35 | 100 |
| Benzonase | 81.6 | 233 |
| Filtration | 48.2 | 138 |
| Inactivation t0 | 110 | 314 |
| Inactivation t 4 h | 154 | 440 |
| Chromato Fractogel-DEAE Flow through | 14.8 | |
| Elution NaCl 350 mM | 30 | 85 | iu represents the number of infectious units.
the flow through represents the material which is not retained on the column and which is therefore directly eluted.

The increase in the adenovirus titres by a factor of 3 to 4 during the inactivation step can be explained by a disintegration of the viruses in the presence of the solvent.

EXAMPLE 2

Preparation of Viruses from the Cell Culture

Example 1 is reproduced with the difference that the cells and the culture supernatant (volume of about 20 l) are harvested 72 h post-infection and the whole is directly subjected to the disruption step.

EXAMPLE 3

Inactivation of Enveloped Viruses 3.1 Validation on a Retrovirus Preparation

The efficiency of the method of inactivation proposed in the present invention is evaluated on recombinant retroviruses expressing the LacZ marker gene encoding the enzyme β-galactosidase. A 20 F500 culture of 293 cells, is prepared. After centrifugation for 8 min at 3000 rpm, the cells are taken up in serum-free medium. The preparation contains $3 \times 10^7$ cells/ml in a volume of 25 ml. The cells are disrupted in a Silverson and then centrifuged for 10 min at 3500 rpm in order to remove the debris. The preparation is then separated into 2, a first half being diluted volume for volume in the benzonase buffer (100 mM Tris, 4 mM $MgCl_2$, 4% sucrose, pH 8.5) in the absence of β-cyclodextrin whereas the second half is treated in a similar manner but in the presence of 3% β-cyclodextrin (1.5% final). The samples are clarified by cascade filtration on Minisart filters (Sartorius) of 5 μm (reference 17594Q), of 1.2 μm (reference 17593Q) and 0.8 μm (reference 17592Q). Each sample is then treated with one volume of 50 mM Tris, 2 mM $MgCl_2$, 2% sucrose, 450 mM NaCl, 0.6% TNBP and 2% Tween® 80, pH 8.5. The retroviral particles are introduced at a final concentration of $1.5 \times 10^6$ infectious particles/ml. The retroviral particle titre is determined after 15 sec, 20 min, 1 h, 2 h and 4 h of incubation either at 4° C. or at room temperature. The titration is carried out by counting the blue cells according to the standard methodology (see for example U.S. Pat. No. 5,747,323).

The results are summarized below:

before treatment: $1.5 \times 10^6$ retrovirus particles/ml room temperature, +β-cyclodextrin, 15 sec of incubation: $<1 \times 10^3$/ml room temperature, −β-cyclodextrin, 15 sec of incubation: $1 \times 10^4$/ml 4° C., +β-cyclodextrin, 15 sec of incubation: $<1 \times 10^3$/ml Beyond 15 sec of incubation, the retroviral particle titres are less than the detection threshold ($10^3$ infectious particles/ml). The results show that the method of inactivation of the invention allows a reduction in the infectivity of the retroviruses by 2 log units in 15 sec. The presence of β-cyclodextrin is advantageous because it enhances the retroviral inactivation by an additional factor of 10.

3.2 Validation of an Adenovirus Preparation Contaminated by BVD Virus

A small scale (18 ml) adenoviral preparation is prepared according to the protocol used in example 1. After clarification by depth filtration in 4 successive steps, 2 ml of a particles solution of BVD are introduced. Then, the inactivation step is carried out in presence of a final concentration of 0.3% TNBT and 1% Tween® 80. The titre in BVD and infectious adenoviral particles is determined after 0 min, 15 min, 60 min and 120 min of incubation at room temperature.

We obtain an inactivation cynetic of BVD virus:

| Time | Titre ($\log_{10}$ TCID50) |
| --- | --- |
| T0 | 5.88 |
| T 5 sec | 5.27 |
| T 15 min | 3.87 |
| T 60 min | <2.57 |
| T 120 min | 1.18 |

That is to say a reduction of 4.7 $\log_{10}$ units after 2 h of inactivation.

EXAMPLE 4

Preparation of Viruses from Complementation Cells

Complementation cells for E1 adenoviral function are cultured in a bioreactor in Excell 525 (JRH Biosciences) medium until to reach a concentration of $1 \times 10^6$ cells/ml and are then infected with an equivalent volume of a prestock of AdTG13383 at the rate of an MOI of about 3. The infected cells are harvested at 72 h post-infection. The culture supernatant (volume of about 20 l) and the whole are directly subjected to the breaking step in order to obtain a crude viral preparation to be purified.

The intracellular viral particles are released after breaking the cells subjected to the mechanical action of 7 to 10 min of a Silverson homogenizer (275 UHLS) set at a rotating speed of 50 Hz (speed of 8.1).

The clarification step is realised by successive filtrations on filters having decreasing porosity, firstly on a 8 μm filter (Sartopure 300PP2 5592501) then on a 5 μm filter (Sartopure 300 PP3 5592542), finally on a filter having a porosity comprised between 3 and 0.8 μm (Sartorius, Sartoclean CA capsule 5621304E9-00-A).

At the clarified viral preparation is added a volume of a buffer allowing the optimum action of benzonase and consisting of 100 mM Tris-HCL, 4 mM $MgCl_2$, 4% saccharose, pH 8.5, further comprising Tween® 80 (Merck reference 8-22187-1000) at a concentration of 2%. The mixture is stirred at room temperature before adding the benzonase in an amount of 10 U/ml (Merck reference 101697) and the reaction is allowed to continue for 2 h at room temperature and with stirring (500 rpm). The clarified viral preparation may also be subjected to the simultaneous action of the benzonase (degradation step of the DNA) and of TNBP/Tween® 80 (inactivation of the enveloped viruses). To do so, TNBP (Aldrich 24-049-40) is added to the precedent preparation at a final concentration of 0.3%. The action of TNBP/Tween® 80 continues with stirring (500 rpm). The titre in infectious units determined after each essential step of the process is summarized in the following table.

| Step | Yield UI-% (total) | Yield UI-% (Step) |
| --- | --- | --- |
| Cells breaking | 100 | — |
| Clarification | 96 | 96 |
| Dnase/Inactivation | 130 | 135 |

The increase in the adenovirus titre by a factor of 1.3 during the inactivation step can be explained by a disintegration of the viruses in the presence of the solvent.

EXAMPLE 5

Validation of an Adenoviral Preparation Contaminated by VSV Virus

A small-scale adenoviral preparation is prepared according to the protocol used in example 4. After breaking and clarification by depth filtration, a solution of VSV particles (ATCC VR-158; 9.9 $\log_{10}$ TCTID50) is introduced in the adenoviral preparation ($2.5 \times 10^{10}$ ui). Then, the inactivation step is carried out in presence of a final concentration of 0.3% TNBP and 1% Tween® 80 simultaneously as the nucleic acids degradation step in presence of 10 U/mi of benzonase (Merck reference 101697). The infectious VSV particles titre is determined on VERO cells according to known techniques (Virology Methods Manual 1996, pp. 35-40, Ed. Mahy and Kangro, Academic Press Ltd. London) after 0 min, 30 min, 60 min and 120 min of incubation at room temperature.

| Time | Titre ($\log_{10}$ TCID 50/ml) |
|---|---|
| T0 | 9.2 |
| T 15 min | 6.8 |
| T 60 min | 5.3 |
| T 120 min | 1.7 |

That is to say a reduction of 7.5 $\log_{10}$ units after 2 h of inactivation.

As a whole, the data show that the process of the invention allows the inactivation of enveloped viruses of a recombinant adenovirus preparation without harming their infectivity and with a total yield higher than 100%.

What is claimed is:

1. A viral preparation comprising non-enveloped viruses obtained according to the method of preparation comprising:
   a) producing the viral preparation in an appropriate cell line;
   b) harvesting the viral preparation from the producer cell line and/or the culture supernatant;
   c) optionally, breaking the cells of the producer cell line;
   d) optionally clarifying;
   e) inactivating enveloped viruses in the said viral preparation in which a sufficient quantity of a solvent comprising tri-n-butyl phosphate (TNBP) of between 0.1% and 0.6% (volume/volume) and TWEEN® 80 at a concentration of between 0.5% and 2% (volume/volume) are introduced into said viral preparation and said solvent and TWEEN® 80 are allowed to act at a temperature between +4°C. to +37° C., at a pH of between 6.5 to 8.5 for a period which is sufficiently long to significantly reduce the quantity of enveloped viruses present in the said viral preparation, wherein said inactivation is capable of preserving at least 80% of the infectious activity of said non-enveloped viruses; and
   f) optionally purifying.

2. The viral preparation according to claim 1, wherein the solvent is allowed to act for a period of between 15 minutes and 24 hours.

3. The viral preparation according to claim 1, wherein the inactivating step is carried out with stirring.

4. The viral preparation according to claim 1, wherein the inactivating step is carried out under conductivity conditions of between 5 and 500 mS/cm.

5. The viral preparation according to claim 1, wherein the quantity of TNBP introduced into the said viral preparation is 0.3% (volume/volume).

6. The viral preparation according to claim 1, wherein the inactivating step is carried out at a temperature of between +15° C. and +25° C.

7. The viral preparation according to claim 1, wherein the inactivating step is carried out at pH 8.5.

8. The viral preparation according to claim 2, wherein the period of time is of between 1 hour and 5 hours.

9. The viral preparation according to claim 4, wherein the conductivity conditions are between 10 and 100 mS/cm.

10. The viral preparation according to claim 1, wherein TNBP at a final concentration of between 0.1% and 0.6% (volume/volume) and Tween®80 at a final concentration of between 0.5% and 2% (volume/volume) are introduced into said viral preparation, said TNBP and said Tween®80 are allowed to act at room temperature at a pH of 8.5 for a period of time between 1 hour and 5 hours, wherein at least 80% of the infectious activity of said non-enveloped viruses is preserved.

11. The viral preparation according to claim 1, wherein said non-enveloped virus is recombinant.

12. The viral preparation according to claim 1, wherein said non-enveloped virus is replication-defective.

13. The viral preparation according to claim 1, wherein in the inactivating step (e), the final concentration of TNBP is 0.6% and the final concentration of TWEEN®80 is 2%.

14. The viral preparation according to claim 1, wherein in the inactivating step (e), the final concentration of TNBP is 0.3% and the final concentration of TWEEN®80 is 1%.

15. The viral preparation according to claim 1 wherein the producing of the viral preparation is from a cell line having undergone an infection carried out at a multiplicity of infection (MOI) of about 1 to 10.

16. The viral preparation according to claim 1, wherein the viral preparation is harvested from the producing cell line and from the culture supernatant.

17. The viral preparation according to claim 1 or 16, wherein the viral preparation is harvested at 48 h or 72 h post-infection.

18. The viral preparation according to claim 1, wherein the breaking of the cells of the producing cell line is carried out by a technique selected from a group consisting of freeze-thaw cycles, enzymatic lysis, chemical means, mechanical means, and any combination thereof.

19. The viral preparation according to claim 18, wherein the mechanical means is selected from the group consisting of ultrasound, attrition, pressure and shear forces, microfluids, the mechanical action of two rollers generating hydraulic and mechanical shear forces, and any combination thereof.

20. The viral preparation according to claim 1, wherein the clarification step comprises successive filtrations carried out on filters of decreasing porosity.

21. The viral preparation according to claim 20, wherein the successive filtrations are carried out on a filter having a porosity of 8 μm, then on a filter having a porosity of 5 μm, then on a filter having a porosity of between 3 μm and 0.8 μm, and then on a filter having a porosity of between 0.8 μm and 0.65 μm.

22. The viral preparation according to claim 1, wherein the clarification step comprises tangential microfiltration.

23. The viral preparation according to claim 1, wherein the purification step comprises an ion-exchange chromatographic step.

24. The viral preparation according to claim 23, wherein the purification step comprises an ion-exchange chromatography and a gel filtration chromatography.

25. The viral preparation according to claim 23, wherein the ion-exchange chromatography is carried out on a support functionalized with quaterny amines.

26. The viral preparation according to claim 24, wherein the gel filtration chromatography is carried out on a support selected from the group consisting of supports comprising allyl dextran-methylene bisacrylamide matrices, ethylene glycol-methacrylate matrices, N-acrylamine hydroxypropanediol matrices and agarose matrices.

27. The viral preparation according to claim 1, wherein said method further comprises a step of degrading nucleic acids.

28. The viral preparation according to claim 27, wherein the step of degrading nucleic acids comprises treatment with benzonase.

29. The viral preparation according to claim 28, wherein the benzonase treatment and the inactivating step (e) are carried out simultaneously after breaking (c) and clarification (d) steps.

* * * * *